(12) United States Patent
Steinman et al.

(10) Patent No.: US 9,259,562 B2
(45) Date of Patent: Feb. 16, 2016

(54) CANNULA

(75) Inventors: Christopher P. Steinman, Sandy, UT (US); Jason A. Belton, Norton, OH (US); Kirk C. Palmerton, Kent, OH (US); Karl H. Beitzel, Canton, OH (US); Rick W. Walker, Stow, OH (US); David Pettinato, Schaumburg, IL (US); Matthew Copithorne, Framingham, MA (US); Brian Otts, Warrior, AL (US); James V. Guarrera, New York, NY (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days.

(21) Appl. No.: 13/545,199

(22) Filed: Jul. 10, 2012

(65) Prior Publication Data
US 2014/0017661 A1    Jan. 16, 2014

(51) Int. Cl.
| A61B 17/122 | (2006.01) |
| A61M 39/02 | (2006.01) |
| A01N 1/02 | (2006.01) |
| A61B 17/00 | (2006.01) |
| A61B 17/28 | (2006.01) |

(52) U.S. Cl.
CPC ......... *A61M 39/0208* (2013.01); *A01N 1/0247* (2013.01); *A61B 17/122* (2013.01); *A61B 2017/0046* (2013.01); *A61B 2017/00969* (2013.01); *A61B 2017/2808* (2013.01)

(58) Field of Classification Search
CPC ............ A61B 17/1227; A61B 17/122; A61B 17/128; A61B 17/1285; A61B 17/08; A61B 17/083; A61B 17/10; A61M 39/28; A61M 39/281; A61M 39/283; A61M 39/284; A61M 39/285; A61M 39/286

USPC ......... 604/244, 164.01, 523, 104–109, 96.01, 604/284.1; 606/151, 157, 158, 218
See application file for complete search history.

(56) References Cited

U.S. PATENT DOCUMENTS

| 1,339,419 | A | * | 5/1920 | Rea | 24/135 K |
| 1,339,420 | A | * | 5/1920 | Rea | 24/135 K |
| 1,566,653 | A | * | 12/1925 | Crotto | 24/135 K |
| 2,262,162 | A | * | 11/1941 | Bock | 24/134 P |
| 3,709,526 | A | * | 1/1973 | Cromie | 285/73 |
| 4,112,944 | A | * | 9/1978 | Williams | 604/244 |
| 4,360,023 | A | * | 11/1982 | Sugita et al. | 606/158 |
| 4,389,034 | A | * | 6/1983 | Suttles | 248/49 |
| 4,437,791 | A | * | 3/1984 | Reynolds | 405/224.2 |

(Continued)

FOREIGN PATENT DOCUMENTS

| EP | 2 263 552 A1 | 12/2010 |
| WO | WO 2012/080390 A1 | 6/2012 |

OTHER PUBLICATIONS

U.S. Appl. No. 13/097,898, filed Apr. 29, 2011.

(Continued)

*Primary Examiner* — Dianne Dornbusch
(74) *Attorney, Agent, or Firm* — Oliff PLC (57) ABSTRACT

A cannula includes a first clamping surface on a closing portion of the cannula, a second clamping surface on a base of a cannula, a connecting structure that connects the closing portion and the base. The connecting structure may allow the closing portion to be rotated around the second clamping surface. The cannula may include a repeatably removable handle.

29 Claims, 6 Drawing Sheets

(56) References Cited

U.S. PATENT DOCUMENTS

| | | | |
|---|---|---|---|
| 4,444,187 A * | 4/1984 | Perlin | 606/158 |
| 4,484,581 A * | 11/1984 | Martin et al. | 606/158 |
| 4,777,950 A * | 10/1988 | Kees, Jr. | 606/158 |
| 4,835,824 A * | 6/1989 | Durham et al. | 24/339 |
| 4,932,955 A * | 6/1990 | Merz et al. | 606/158 |
| 4,943,298 A * | 7/1990 | Fujita et al. | 606/158 |
| 4,961,743 A * | 10/1990 | Kees et al. | 606/158 |
| 5,053,045 A * | 10/1991 | Schmidt et al. | 606/157 |
| 5,074,870 A * | 12/1991 | von Zeppelin | 606/158 |
| 5,571,125 A * | 11/1996 | Chadwick | 606/157 |
| 5,683,405 A * | 11/1997 | Yacoubian et al. | 606/158 |
| 5,728,115 A * | 3/1998 | Westcott et al. | 606/151 |
| 5,911,728 A * | 6/1999 | Sepetka et al. | 606/151 |
| 5,921,996 A | 7/1999 | Sherman | |
| 5,984,934 A * | 11/1999 | Ashby et al. | 606/151 |
| 6,088,889 A * | 7/2000 | Luther et al. | 24/489 |
| 6,776,783 B1 * | 8/2004 | Frantzen et al. | 606/151 |
| 7,077,851 B2 * | 7/2006 | Lutze et al. | 606/158 |
| 7,144,402 B2 * | 12/2006 | Kuester, III | 606/158 |
| 7,581,292 B2 * | 9/2009 | Votel | 24/545 |
| 7,588,585 B2 * | 9/2009 | Gold et al. | 606/206 |
| 7,645,285 B2 * | 1/2010 | Cosgrove et al. | 606/151 |
| 7,824,848 B2 | 11/2010 | Owen et al. | |
| 8,361,108 B2 * | 1/2013 | Gold et al. | 606/206 |
| 2004/0111104 A1 * | 6/2004 | Schein et al. | 606/153 |
| 2006/0217746 A1 * | 9/2006 | Krolman | 606/151 |
| 2009/0123993 A1 | 5/2009 | Banes et al. | |
| 2010/0096570 A1 * | 4/2010 | Kashmirian et al. | 251/9 |
| 2010/0268161 A1 * | 10/2010 | Traversaz | 604/151 |
| 2012/0276519 A1 * | 11/2012 | Kravitz et al. | 435/1.2 |
| 2012/0277681 A1 * | 11/2012 | Kravitz et al. | 604/175 |
| 2012/0277687 A1 * | 11/2012 | Kravitz et al. | 604/246 |
| 2013/0006198 A1 * | 1/2013 | Traversaz | 604/250 |

OTHER PUBLICATIONS

U.S. Appl. No. 13/097,789, filed Apr. 29, 2011.
U.S. Appl. No. 13/283,166, filed Oct. 27, 2011.
Apr. 17, 2014 Search Report issued in International Patent Application No. PCT/US2013/049558.
Apr. 17, 2014 Written Opinion issued in International Patent Application No. PCT/US2013/049558.
Sep. 4, 2014 Written Opinion issued in International Patent Application No. PCT/US2013/049558.
Oct. 30, 2014 Notification of Transmittal of the International Preliminary Report on Patentability issued in International Application No. PCT/US2013/049558.

* cited by examiner

CANNULA

BACKGROUND

Related technical fields include cannulas and clamping methods, including cannulas and clamping methods for perfusing one or more organs or tissue to monitor, treat, sustain and/or restore the viability of the organ(s) or tissue and/or for transporting and/or storing the organ(s) or tissue.

Various devices have been developed that couple the anatomy of an organ being perfused to a machine or other equipment such as that described in U.S. Pat. No. 7,824,848, the entire disclosure of which is hereby incorporated by reference. Such devices are typically referred to as perfusion clamps or simply cannulas. Although the term cannula in general use has other meanings, the term cannula is used generically throughout this specification to refer to a clamp or other device that provides a connection through which fluid flow may be established.

Figure 1:
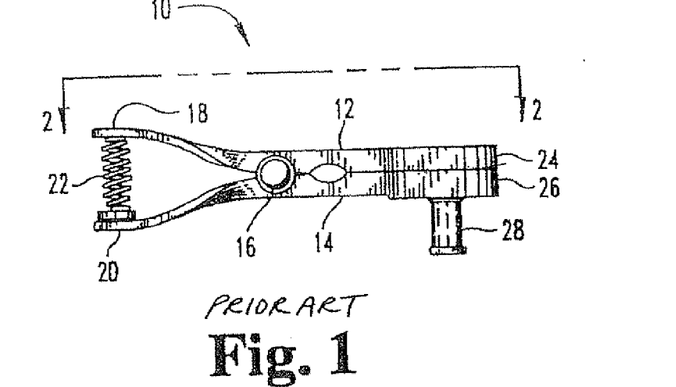
FIGS. 1-3 illustrate a cannula of the prior art.
Figure 2:
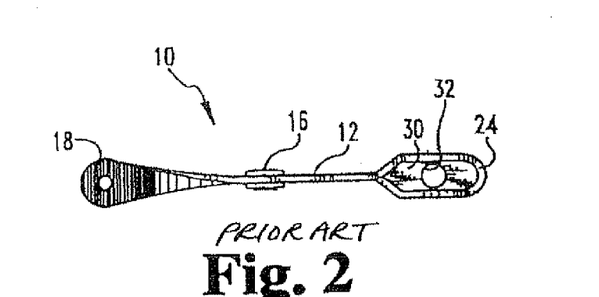
Figure 3:
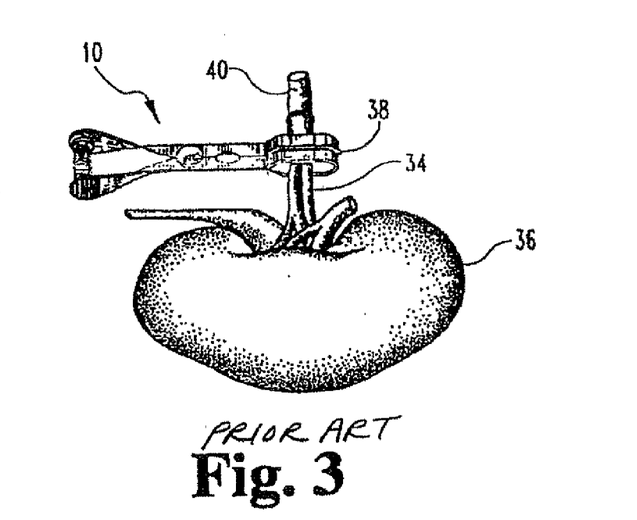

A type of cannula as described in U.S. Pat. No. 5,728,115 to Westcott et al., which is hereby incorporated by reference, is shown in FIGS. 1-3. A clamping device (cannula) 10 is used to couple a perfusion device to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an elongated, hollow, annular, integral clamp head 24, while the distal end of the member 14 includes an elongated, hollow, annular, integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in a clamping relationship unless an external compressive force is applied to the handles 18 and 20. A lumen 32 extends through the nipple 28.

In use, the clamp 10 is attached to a blood vessel of a donor organ such as the renal aorta 34 of a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24, A catheter 40 may then be attached to the nipple 28 in order to provide perfusion of liquid through the lumen 32 and into the renal aorta 34.

SUMMARY

The cannula as described above is difficult and/or cumbersome to use because the spring 22 biases the clamp heads 24 and 26 together. The problem is at least two-fold. First, a user must actively hold open the cannula 10 in order to insert the renal aorta into the clamp head 24. This leaves one hand available for the user to manipulate the renal aorta or requires the help of a second user. Also, this configuration results in a force being applied by default, and that force is not adjustable because it is determined by the spring constant and the thickness of any clamped tissue (neither of which is adjustable by a user). Second, the clamp head 24 obscures the user's view of and restricts access to the clamp head 26, in particular the interior passage and clamping surface.

The cannula as described above also is cumbersome because it includes handles 18 and 20. The handles are necessary to open the cannula, but are otherwise extraneous. When used in conjunction with an organ perfusion apparatus, the handles may be too large or in the way when the organ is disposed in an organ perfusion apparatus, which could result in damage if the handles contact delicate tissue. The cannula described above also will engage any blood vessel between heads 24 and 26 in an uneven manner because the portion of the heads 24 and 26 nearest the pin 16 will typically contact the blood vessel before portions of the heads 24 and 26 further away from the pin 16. Such uneven engagement may result in an unequal distribution of force that may damage the blood vessel. Also, the nipple 28 in the cannula as described above extends perpendicular from the clamping surfaces. This configuration may be cumbersome or unacceptable for use in tight spaces. The nipple 28 may also leak.

A cannula may include a first clamping surface on a closing portion of the cannula, a second clamping surface on a base of the cannula, and a connecting structure that connects the closing portion and the base. The connecting structure may allow the closing portion to be rotated around the second clamping surface. Preferably, the first clamping surface and the second clamping surface are configured to secure tissue between the first clamping surface and the second clamping surface. The closing portion may preferably be rotatable at least 90°, preferably at least 180° or 360° around the second clamping surface. When rotating around the second clamping surface, the first clamping surface preferably remains facing the base. Preferably, the closing portion is rotatable about the base in the open position and the closing portion is not rotatable about the second clamping surface in the closed position.

The connecting structure may be configured to bias the closing portion towards the base and to bias the closing portion away from the base.

The cannula preferably includes at least one passage in the closing portion and/or the base. Preferably, a passage in the closing portion provides fluid communication between an opening in the first clamping surface and another opening, which preferably provides an external fluid connection, for example to perfusion apparatus. The passage in the closing portion may be straight or may include a turn, and the passage may change size and/or shape to transition from the opening in the first clamping surface to the other opening. Preferably, a passage in the base connects an opening in the second clamping surface and a second opening in the base, which in combination allow for a free end of vasculature to pass through the second opening and then through the opening in the second clamping surface.

Exemplary implementations may include a handle that can be repeatably attached to and removed from the cannula. Preferably, the removable handle has a length that is more than half of the overall length of the cannula. The removable handle may be attached in various ways, for example by way of a releasable snap fit or by way of mating threads. Preferably, the cannula is fully functional for providing fluid flow to or from a cannulated vasculature with or without the handle. A removable handle provides advantages. For example, cannulas may be small relative to the size of a user's hands due to the size of the vasculature to be cannulated. For example, vasculature can be on the order of about three to seven millimeters in diameter. The resulting geometry for cannulating such a vasculature can be quite small relative to a user's hands, resulting in difficulty manipulating such relatively small geometry. By adding a handle, the cannula can be more easily manipulated by a user. However, the addition of a handle makes the cannula much larger, which may result in difficulties in use, where the handle may get in the way of other devices (such as portions of an organ perfusion apparatus). By including a removable handle, ease of use and/or manipulation can be improved with the handle on the cannula while a relatively small size can be achieved with the handle removed.

Exemplary implementations include a method of cannulating vasculature including inserting the vasculature through a hole in a cannula, folding back a portion of the vasculature to expose an interior of the vasculature, engaging an external surface of the portion with a first clamping surface of the cannula; and engaging an internal surface of the portion with a second clamping surface of the cannula. Preferably, the angle that the vasculature is folded back is approximately 135°.

Exemplary methods may include manipulating a cannula by gripping a handle with a user's hand and moving at least one clamping surface with the thumb on the same hand. The thumb may engage a surface, such as a textured surface, to initiate the movement. Moving the clamping surface may include rotating the clamping surface around a second clamping surface, moving the clamping surface towards the second clamping surface and/or moving the clamping surface away from the second clamping surface. Such movement may occur before the cannula has been used to clamp vasculature or after the cannula has been unclamped from the vasculature. Exemplary methods may also include attaching a handle to a cannula before clamping vasculature with the cannula, or removing vasculature from the cannula, and/or removing a handle from a cannula once vasculature is clamped to the cannula.

BRIEF DESCRIPTION OF THE DRAWINGS

Exemplary implementations are described herein with reference to the following figures wherein.

DETAILED DESCRIPTION OF EMBODIMENTS

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference in their entireties.

Ideally organs would be procured in a manner that limits their warm ischemia time to essentially zero. Unfortunately, in reality, many organs, especially from non-beating heart donors, are procured after extended warm ischemia time periods (e.g., 45 minutes or more). The machine perfusion of these organs at low temperature has demonstrated significant improvement (Transpl Int 1996 Daemen). Numerous control circuits and pumping configurations have been utilized to achieve this objective and to machine perfuse organs in general. See, for example, U.S. Pat. Nos. 5,338,662 and 5,494, 822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thome et al.; U.S. Pat. Nos. 5,285,657 and 5,476,763 to Bacchi et al.; U.S. Pat. No. 5,157, 930 to McGhee et al.; and U.S. Pat. No. 5,141,847 to Sugimachi et al., which are hereby incorporated by reference in their entireties.

The cannulas and clamping methods described herein may be used in conjunction with apparatus and methods described in U.S. Pat. Nos. 6,014,864, 6,183,019, 6,241,945 and 6,485, 450 to Owen, which are hereby incorporated by reference in their entireties. While these apparatus and methods are related to organ recovery and transplantation, the cannulas and clamping methods described herein may also be used in various other medical procedures and with various other medical equipment where clamping with fluid flow is desired. Thus, the cannulas and clamping methods described herein are not limited to the applications described below in conjunction with the exemplary implementations.

Figure 4:
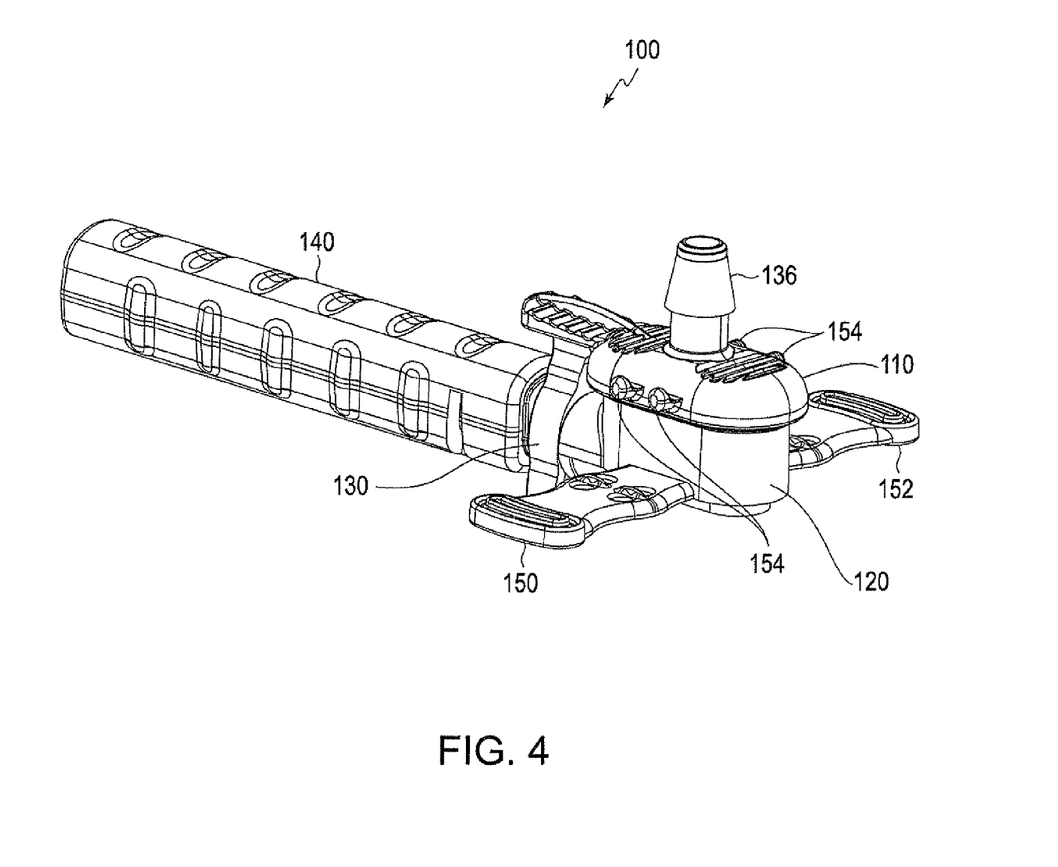
FIG. 4 illustrates a cannula in a closed state.

FIG. 4 shows a perfusion clamping apparatus or cannula 100 according to a first exemplary implementation. The cannula 100 is capable of connecting one or more blood vessels of an organ or tissue to a perfusion machine or system (not shown), for example, by connection to tubing of the perfusion machine or system. All medical fluid contact surfaces are preferably formed of or coated with materials compatible with the medical fluid used, preferably non-thrombogenic materials. For convenience, the term "organ" will be used herein to mean organ and/or tissue, except as otherwise specified.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. Further, the medical fluid may be or include blood or blood products.

A cannula 100 as described herein may be used in various advantageous ways. The cannula 100 may advantageously be manipulated with a single hand of a user. The user may grip the handle 140 with one hand and manipulate the closing portion 110 with a thumb on that same hand, which may rotate the closing portion 110 towards or away from an opened or closed state. The user may advantageously attach the handle 140 if, for example, the handle 140 is needed to grip the cannula 100 or the user may remove the handle 140 if, for example, space constraints do not allow the cannula 100 to fit the space available with the handle 140 attached. After the handle 140 has been removed, it may later be attached again. The handle 140 may be repeatably attached or removed for any reason.

The cannula 100 may be opened or closed such that the first clamping surface 112 and the second clamping surface 122 are moved together or apart while the clamping surfaces remain parallel or nearly parallel. This may be advantageous in that any clamping force can be evenly applied or removed to avoid damage to clamped tissue. Such movement can be achieved with a single hand. For example, a user can grip the handle 140 with one hand while pressing down on the closing portion 110 with the thumb of the same hand. Alternatively, while the handle is gripped in one hand, the user can move the first clamping surface 112 away from the second clamping surface 122 by inserting the user's thumb under the closing portion to lift the closing portion 110.

The cannula 100 can be attached to an external fluid conduit. Preferably, the cannula 100 may be connected to an external fluid conduit after vasculature has been cannulated, but the cannula 100 may be connected to an external fluid conduit prior to cannulation as well. Connection to an external fluid conduit may be achieved by connecting the fluid conduit to a nipple 136. An external fluid conduit may provide fluid communication for any use. For example, the external fluid conduit may provide a connection between the cannula 100 and an organ perfusion machine.

Figure 5:
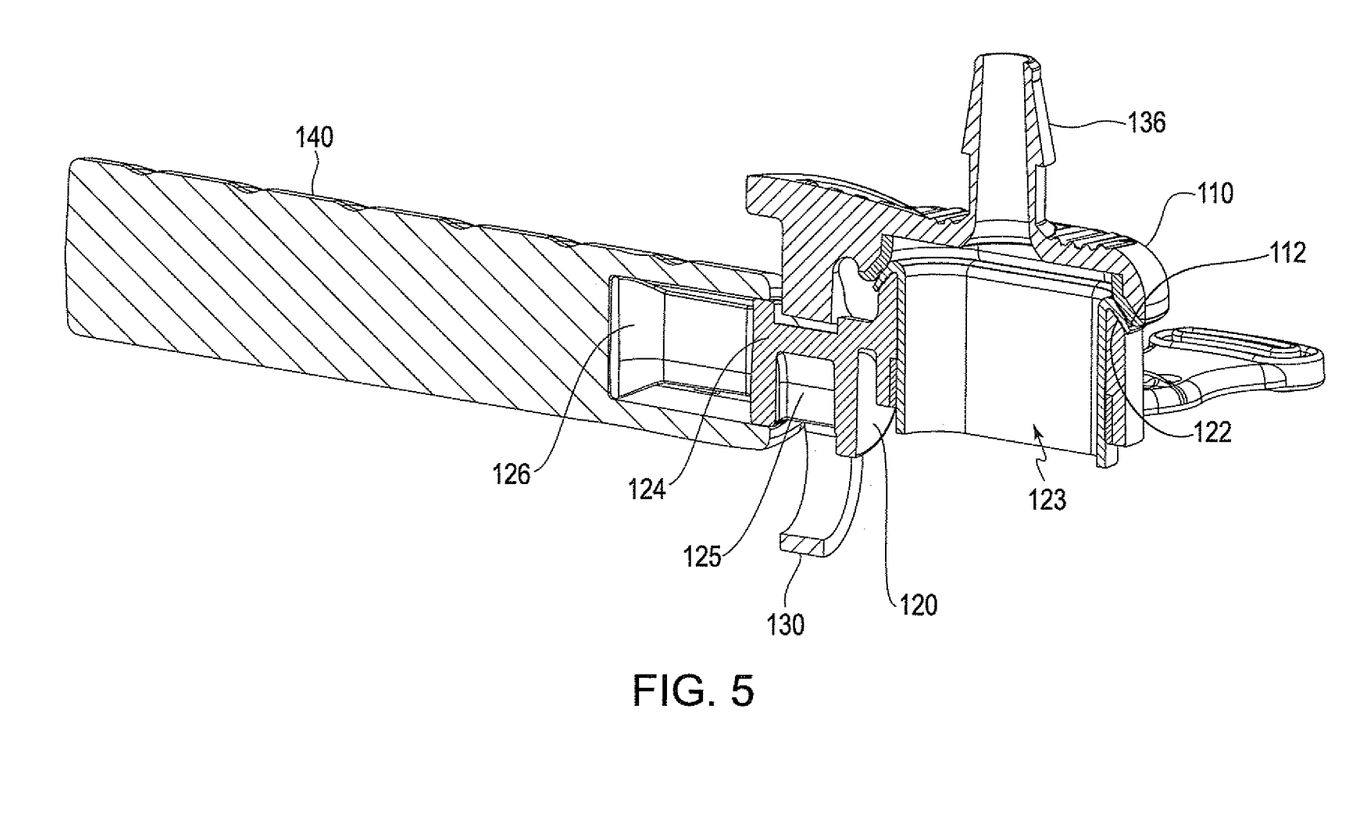
FIG. 5 illustrates a cross section of a cannula in a closed state.

The cannula 100 shown in FIG. 4 and FIG. 5 is in a closed condition. In a closed condition, a first clamping surface 112 on the closing portion 110 and a second clamping surface 122 on the base 120 are in close proximity to or in contact with one another. Preferably, in the closed condition, the first clamping surface 112 and the second clamping surface 122 may provide a gap between the surfaces to accommodate tissue such as vasculature. The first clamping surface 112 and the second clamping surface 122 may be made from relatively soft (such as elastomeric) material or relatively hard material (such as plastics or metal). Furthermore, one or both of the first clamping surface 112 and the second clamping surface 122 may include ridges or a stair step-like structure, which may help to retain a clamped tissue or vasculature.

The base 120 may include a connecting structure 130 that connects the closing portion 110 to the base 120. Preferably, the connecting structure 130 allows the closing portion 110 and/or the first clamping surface 112 to be rotated around the base 120 and/or the second clamping surface. As shown in the figures, the connecting structure allows a full 360 degrees of rotation. However, varying amounts of rotation are contemplated by the broad inventive principles described herein. For example, the connecting structure 130 may allow 90 degrees of rotation, 180 degrees of rotation, or any other amount of rotation from 0-360 degrees as dictated by the needs of a user. Such movement can be achieved with one hand of a user. For example, the user can grip the handle 140 in one hand while applying a rotational force on the closing portion 110 with the thumb on that same hand. The rotational force is preferably applied when the closing portion is in an open position.

As shown, the first clamping surface 112 defines a face of the closing portion 110. As the closing portion 110 is rotated around the base 120, the face remains facing the base. However, additional structure could be provided that allows the face to change orientation if desired by a user and still be within the broad inventive principles described herein.

Figure 6:
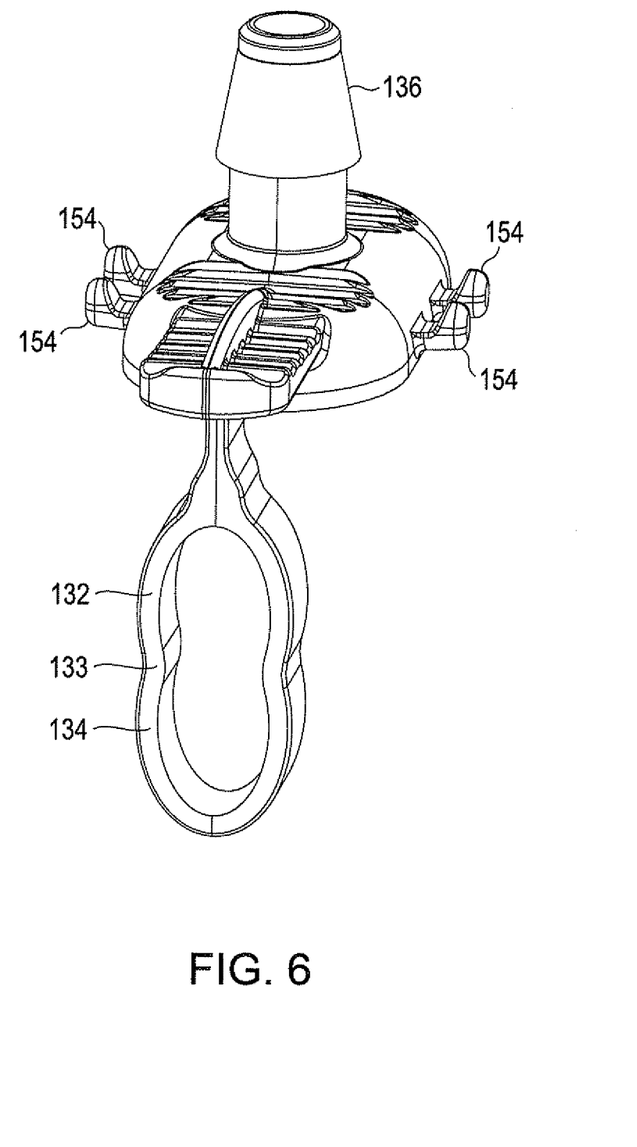
FIG. 6 illustrates a portion of a cannula.

As shown in FIG. 6, the connecting structure 130 may include a first lobe 132 and a second lobe 134. Together, these lobes form an approximately figure-eight shape with a narrowing portion 133 between the lobes. When interacting with an axle 124 (as shown at least in FIG. 5), the lobes act to bias or hold the closing portion 110 towards or away from the base 120 depending on the location of the axle 124 with respect to the lobes. If the axle 124 is beyond an inflection point such that more of the axle 124 is within the first lobe 132 than the second lobe 134, the base will be biased towards a closed position, whereas if the axle 124 is beyond the inflection point such that more of the axle 124 is within the second lobe 134 than the first lobe 132, the base will be biased towards an open position. The biasing between lobes is due to the narrowing portion 133. Depending on the relative size of the lobes 132, 134 and the axle 124, a biasing force may or may not continue to be applied in the closed and open positions. For example, if the diameter of the axle 124 is slightly larger than the inner diameter of one of the lobes 132, 134, then there will be at least a slight interference fit which will continue to bias the axle 124 to whatever position it is currently in. However, if the diameter of the axle 124 is smaller than the inner diameter of one of the lobes 132, 134, then there will be a loose fit such that the biasing force will cease at an intermediate point between the inflection point and the closed or open position. Both lobes 132, 134 may have an interference fit, both lobes 132, 134 may have a loose fit, or there may be a combination of loose and interference fit. The axle 124 can be shifted between the lobes 132, 134 with one hand of the user. For example, while the user grips the handle 140 in one hand, the thumb of the same hand can either press down or lift up the closing portion 110, which may result in the axle 124 moving from one lobe to another.

Additionally, the narrowing portion 133 may interact with an indentation or opening 125 of the axle 124 (as shown in FIG. 5) to maintain the closing portion 110 in an intermediate position. If the closing portion is rotated 90 degrees from the closed position, one side of the narrowing portion 133 may engage the opening 124. Doing so will tend to keep the closing portion 110 rotated 90 degrees and between the biased open (second lobe 134) position and the biased closed (first lobe 132) position. Of course, more than one opening 125 may be included, or a single opening 125 may be positioned, such that the closing portion 110 is maintained in any rotational position. For example, the rotational position could correspond to 45 degrees, 60 degrees, 75 degrees or any other angle, or combination of angles, as dictated by the needs of a user. The closing portion 110 can be placed in the intermediate position using a single hand. For example, the handle 140 can be gripped in a user's hand and the thumb on that hand can apply a rotational force to the closing portion 110 to rotate the closing portion 110 around the base 120 until the base 110 is rotated to the appropriate rotational angle. Once at that angle, the user can adjust the position of the closing portion 110 with the thumb such that the narrowing portion 133 engages the opening 125 and the closing portion 110 is thus in the intermediate position.

As can be seen in FIG. 5, the first clamping surface 112 and the second clamping surface 114 may be formed as complementary surfaces. For example, FIG. 5 illustrates the first clamping surface 112 as forming an interior acute angle whereas the second clamping surface 122 is illustrated as an exterior acute angle. Alternatively, both of the clamping surfaces can be described as approximately frustoconical sections. When the first clamping surface 112 and the second clamping surface 122 are in a closed condition, the complementary nature of the surfaces tends to prevent the closing portion 110 from being rotatable around the base 120, but in the open position, the closing portion 110 is freely rotatable. The first clamping surface 112 and the second clamping surface 114 may be made from soft elastomers to reduce injury and/or trauma to the cellular structure of a cannulated vasculature.

As illustrated in FIG. 5, the base 120 includes a passage 123 with two openings. One of the openings is shown as surrounded by the second clamping surface 122 and the other opening is shown on a side of the base 120 opposite from the second clamping surface 122, The passage 123 is shown as having an approximately oval shaped cross section, but other shapes are contemplated in the broad inventive principles described herein. For example, the passage 123 could have a circular cross section. In use, the passage 123 provides a space through which vasculature may pass to be clamped between the first clamping surface 112 and the second clamping surface 122. Preferably, the vasculature is inserted through the passage 123 with a free end of the vasculature at or near the second clamping surface 122. Then, the vasculature can be folded back such that an internal surface of the vasculature is exposed and the internal surface can be contacted by the first clamping surface 112 when the cannula 100 is in a closed position. Preferably, the vasculature is folded back more than 90 degrees and more preferably approximately 135 degrees. The amount that the vasculature is folded back may be defined by an angle of the first clamping surface 112 and/or the second clamping surface 122. For example, and angle of the second clamping surface may be between 105 degrees and 150 degrees when defined between the second clamping surface 122 and an axis of the passage 123. Alternatively, the angle may be defined between an interior surface of the passage 123 and the clamping surface 122, which may be between 30 degrees and 60 degrees. If the angle is approximately 135 degrees, the contact area of the first clamping surface 112 and the second clamping surface 114 may be maximized while maintaining an evenly distributed clamping force. In this context, approximately is intended to encompass standard manufacturing tolerances for angles, but includes a tolerance of at least plus or minus ten degrees. The amount the vasculature is folded back will generally be dictated by an angle formed by the first clamping surface 112 and/or the second clamping surface 122.

FIG. 5 also illustrates a connection for tubing, such as a nipple 136. The nipple 136 includes part of an internal passage within the closing portion 110. The first clamping surface 112 approximately surrounds one opening of the internal passage and a second opening of the internal passage is at or near an end of the nipple 136. Although a nipple is illustrated in the figures, other connection types are contemplated by the broad inventive principles described herein. For example, standard leer geometry or other suitable structure may be used instead of a nipple.

Figure 8:
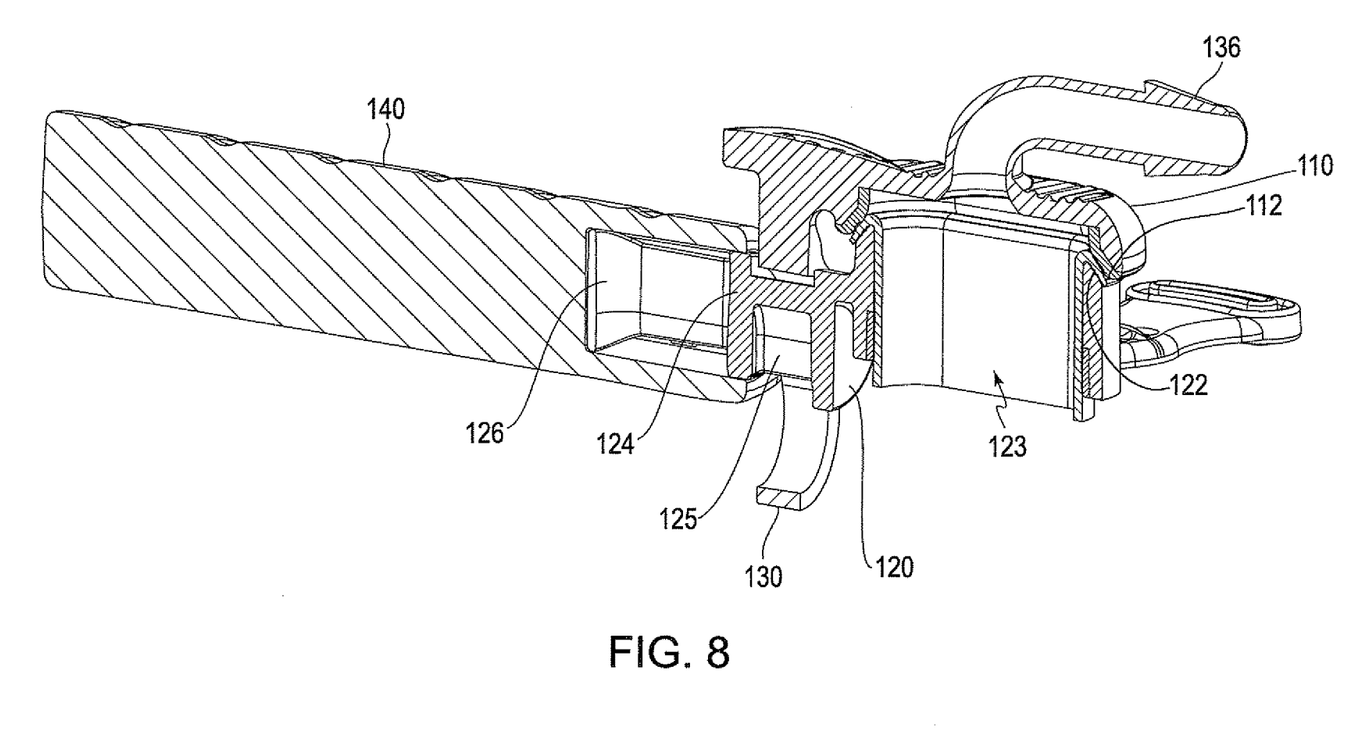
FIG. 8 illustrates a cross section of a cannula in a closed state.

As shown in FIG. 5, the internal passage of the closing portion 110 changes diameter but is straight. However, the internal passage may include an internal bend, such that the nipple 136 is at an angle to the first clamping surface 112. As shown in FIG. 8, the internal passage as it passes through the nipple 136 is at an angle of approximately 90 degrees with respect to the internal passage of FIG. 5. With such a bend, a surface defined by the opening at the end of the nipple 136 is approximately perpendicular to the first clamping surface 112, which results in an axis of the opening at the end of the nipple 136 being approximately parallel an axis of rotation of the closing portion 110 about the base 120. The axle 124 may define such an axis of rotation. Alternatively, the nipple 136 may be disposed on a side of the closing portion 110, resulting in a similar relative position between the surface defined by the end of the nipple 136 and the first clamping surface 112. Also, other configurations may result in other exemplary angles between the end of the nipple 136 and the first clamping surface 112 as dictated by the needs of a user or by the geometry of a device where the cannula 100 is used. Exemplary angles may be, but are not limited to, 15 degrees, 30 degrees, 45 degrees, 60 degrees or 75 degrees.

As illustrated in FIG. 4, the cannula 100 may include a first latching member 150 and/or a second latching member 152. The first latching member 150 and the second latching member 152 may preferably be made from an elastomeric material, preferably with good tear resistance and compression set properties, which may include medical grade silicone rubber or synthetic polyisoprene or equivalents. The latching members include holes that mate with the protrusions 154. Alternatively, the positions of the holes and protrusions may be reversed such that the protrusions are on one or both of the latching members. The latching members may include a series of holes that provide the ability to apply varied clamping forces urging the closing portion 110 towards the base 120. Two sets of holes are illustrated, which may allow for two different clamping forces, but any number of holes or sets of holes are contemplated in the broad inventive principles described herein. The latching members 150, 152 can preferably be disengaged with a single hand of a user. For example, the user can grip the handle 140 in one hand and use the thumb on that hand to disengage one or both of the latching members 150, 152. The user can insert their thumb between a latching member 150, 152 and the closing portion 110 and apply a force to separate the latching member 150, 152 from the protrusions 154. Alternatively, the user can use both hands to manipulate the latching members 150, 152. Preferably, the latching members 150, 152 can be repeatably actuated as desired by the user.

Figure 7:
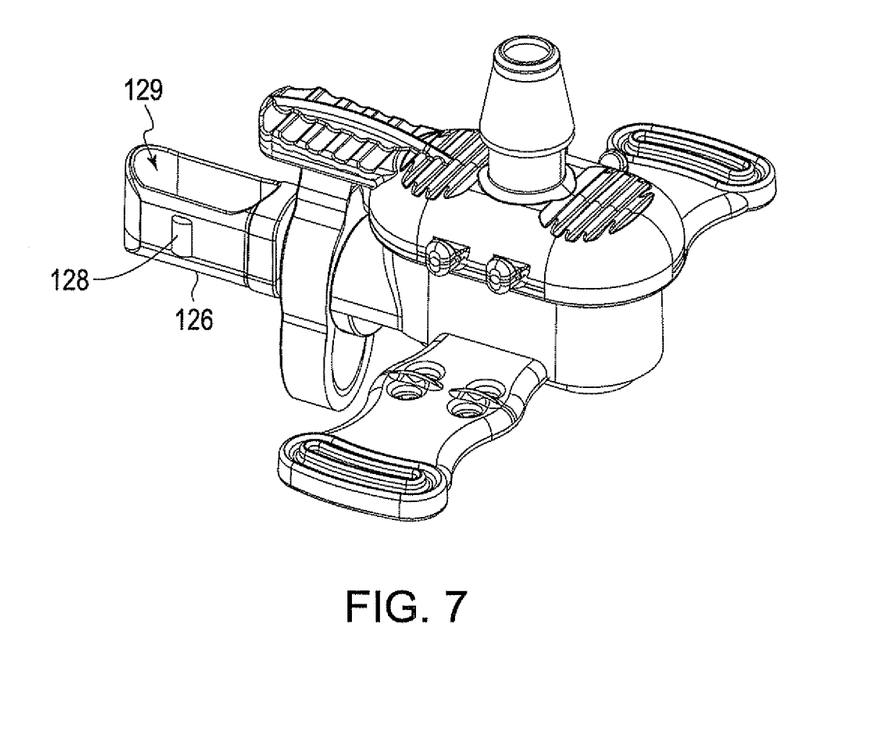
FIG. 7 illustrates a cannula in a closed state with a handle removed.

FIGS. 4 and 5 show a handle 140 disposed on the cannula 100. Preferably, the cannula 100 is fully functional for cannulating and/or providing flow to vasculature with and without the handle in place. FIG. 7 shows the cannula 100 without the handle 140. Preferably, the handle 140 may be provided such that the handle 140 can be repeatably attached to and removed from the cannula 100. As described below, the handle shown in the figures is attached by way of a releasable snap fit, but other structures are contemplated in the broad inventive principles described herein. For example, the handle could be attached by way of mating male and female threads or a frictional fit other than a snap fit.

As shown in FIGS. 4, 5 and 7, the handle 140 may be attached to the cannula 100 by way of a snap fit. FIG. 7 illustrates a protrusion 128 that mates with an indentation or opening 142 (as shown in FIG. 4) when the insert 126 is inserted into the handle 140. The insert 126 may be made flexible by way of the hollow portion 129 in the insert 126. As shown in the figures, the hollow portion 129 is an approximately oval-shaped hole through the insert 126 but other shapes are contemplated as well. The hollow portion 129 provides flexibility to allow the protrusion 128 to deflect when the insert 126 is inserted into or removed from the handle 140. However, the broad inventive principles described herein encompass other ways in which a snap fit may be made repeatably releasable, as would be understood by one of ordinary skill.

Each of the components of the cannula 100 can be made from any number of materials based upon the broad inventive principles described herein. Some of the components may preferably made through injection molding of plastic; however, other materials are contemplated as well.

The handle may be more than half of an overall length of the cannula 100. Preferably, the handle is approximately three quarters of the overall length of the cannula. For example, the handle maybe between 2 and 6 inches long, preferably about 3 to 3.5 inches. However, any length of handle is within the broad inventive principles discussed herein. Preferably, the handle has an oval shaped cross section, but any shape can be chosen based upon the needs of the user. If the handle has an oval shaped cross section, the minor diameter is preferably approximately 0.5-0.6 inches and the major diameter is preferable approximately 0.5-0.7 inches. The handle may also include gripping features that are shown as approximately oval shaped depressions and/or protrusions, although other types of gripping features are contemplated. Preferably, the gripping features are about 0.05-0.2 inches, such as about 0.1 inches high and/or deep. Including such gripping features is advantageous because users are likely to use the cannula 100 while wearing medical gloves, which can result in relatively low friction, and the gripping features improve the user's ability to grip the cannula 100.

The closing portion 110 may include ridges or other textures, preferably on a side opposite the first clamping surface 112, for improved gripping or manipulation. For example, as show in FIG. 4, the closing portion 110 may include several transverse ridges as well as one or more longitudinal ridge on a handle side of the nipple 136. One or more of these ridges may allow a user to readily manipulate the position of the closing portion 110 with a thumb of the hand gripping the handle 140. The user can grip the handle 140 in one hand and engage the ridges or other textures with the thumb of that hand. The ridges may be used in any of the one-handed manipulations discussed above.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. A cannula comprising:
    a first clamping surface on a closing portion of the cannula;
    a second clamping surface on a base of the cannula; and
    a handle that is connected to the base and that extends from the lyase in an axial direction; and
    a connecting structure that connects the closing portion and the base, wherein
    the connecting structure is configured to allow the closing portion to rotate around the second clamping surface,
    the closing portion rotates around the second clamping surface such that an axis of rotation of the closing portion is parallel to the axial direction of the handle, and
    the first clamping surface and the second clamping surface are configured to mutually cooperate to clamp tissue between the first clamping surface and the second clamping surface.

2. The cannula according to claim 1, wherein the closing portion is rotatable 360° around the second clamping surface.

3. The cannula according to claim 1, wherein
    the first clamping surface remains facing the base as the closing portion is rotated around the second clamping surface.

4. The cannula according to claim 1, wherein the connecting structure is configured to bias the closing portion towards the base and to bias the closing portion away from the base.

5. The cannula according to claim 4, wherein the closing portion is rotatable about the second clamping surface in the open position and the closing portion is not rotatable about the second clamping surface in the closed position.

6. The cannula according to claim 4, wherein the connecting structure comprises a portion that is shaped approximately like a figure-eight.

7. The cannula according to claim 1, further comprising a handle that is configured to be repeatably attached to and removed from the cannula.

8. The cannula according to claim 7, wherein the handle is configured to be repeatably attached to and removed from the base.

9. The cannula according to claim 1, wherein the first clamping surface defines an interior acute angle and the second clamping surface defines an exterior acute angle.

10. The cannula according to claim 1, wherein the cannula is configured to include at least a fully open position, a fully closed position and an intermediate position between the fully open position and the fully closed position, and the connecting structure is configured to maintain the cannula in the intermediate position.

11. The cannula according to claim 1, wherein the base includes a first passage with a first opening and a second opening and the second clamping surface is disposed around the first opening, and
    the closing portion includes a second passage with a third opening and a fourth opening and the first clamping surface is disposed around the third opening.

12. The cannula according to claim 11, wherein the second passage is straight.

13. The cannula according to claim 11, wherein the second passage includes a bend.

14. The cannula according to claim 13, wherein an axis of the first passage and an axis of a portion of the second passage adjacent the fourth opening are at approximately right angles to one another.

15. The cannula according to claim 14, wherein the axis of said portion of the second passage is approximately parallel to an axis of rotation of the closing portion around the base.

16. The cannula according to claim 1, further comprising a latch configured to fasten the cannula in a closed position.

17. The cannula according to claim 16, wherein the latch is configured to exert a force urging the first clamping surface and the second clamping surface together when the latch is in a latched position.

18. The cannula according to claim 1, further comprising:
    a handle with a length parallel to an axis of rotation defined by rotation of the closing portion around the second clamping surface; and
    a grip on the connecting structure configured to be engaged by a thumb on a user's hand when the handle is gripped by the hand,
    wherein the grip is configured to facilitate rotation of the closing portion around the second clamping surface.

19. The cannula according to claim 1, wherein the connecting structure allows the closing portion to be rotated around the second clamping surface about multiple degrees of freedom.

20. The cannula according to claim 1, wherein the base is intersected by an axis of rotation of the closing portion.

21. The cannula according to claim 1, wherein:
    the connecting portion is disposed in a rear direction from the base, and the connecting structure allows the closing portion to be rotated in a plane perpendicular to the rear direction.

22. A cannula comprising:
    a first clamping member having a first clamping surface and defining a flow passage through the first clamping member, the flow passage having a first opening and a second opening,
    a second clamping member having a second clamping surface;
    a connecting structure that connects the first clamping surface and the second clamping surface such that the first clamping surface and the second clamping surface are movable with respect to one another between an open position and a closed position wherein, in the closed position the first clamping surface and the second clamping surface are configured to clamp an open end of a blood vessel therebetween; and
    a removable handle that is configured to be repeatably attached to and removed from the cannula.

23. The cannula according to claim 22, wherein
    the cannula has an overall length that includes the handle, and the handle has a length that is more than half of the overall length.

24. The cannula according to claim 22, further comprising
a protrusion on one of the connecting structure and the handle; and
a hole disposed in the other of the connecting structure and the handle,
wherein the protrusion is disposed within the hole when the handle is attached to the cannula.

25. The cannula according to claim 24, wherein the protrusion fits into the hole with a releasable snap fit.

26. The cannula according to claim 24, wherein the protrusion and the hole include mating threads.

27. The cannula according to claim 22, wherein the cannula is fully functional for providing fluid flow to or from cannulated vasculature with or without the removeable handle attached to the cannula.

28. The cannula according to claim 22, wherein
the first clamping surface and the second clamping surface each comprise annular shaped surfaces configured to mate with each other.

29. The cannula according to claim 22, wherein the flow passage is a closed flow passage.

* * * * *